United States Patent [19]

Rohner

[11] Patent Number: 6,073,501

[45] Date of Patent: *Jun. 13, 2000

[54] APPARATUS AND METHOD FOR SEMICONDUCTOR WAFER PROCESSING WHICH FACILITATE DETERMINATION OF A SOURCE OF CONTAMINANTS OR DEFECTS

[75] Inventor: Don R. Rohner, Austin, Tex.

[73] Assignee: Advanced Micro Devices, Inc., Sunnyvale, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/879,510

[22] Filed: Jun. 20, 1997

[51] Int. Cl.$^7$ .................................................. G01N 21/88
[52] U.S. Cl. ............................................................. 73/865.8
[58] Field of Search ................................ 73/865.8, 865.9; 414/935, 937, 938, 939, 941

[56] References Cited

U.S. PATENT DOCUMENTS

| | | |
|---|---|---|
| 4,813,845 | 3/1989 | Swain . |
| 4,923,054 | 5/1990 | Ohtani et al. . |
| 5,240,866 | 8/1993 | Friedman et al. . |
| 5,317,380 | 5/1994 | Allemand . |
| 5,647,724 | 7/1997 | Davis, Jr. et al. . |

*Primary Examiner*—Robert Raevis
*Attorney, Agent, or Firm*—Conley, Rose & Tayon, P.C.; Robert C. Kowert; Kevin L. Daffer

[57] ABSTRACT

An apparatus and method are presented for performing a wafer fabrication operation upon each of a plurality of semiconductor wafers which facilitate determination of a source of semiconductor wafer contaminants or defects. A wafer fabrication tool of the present invention includes a process chamber for processing a semiconductor wafer and a wafer handling system for transporting the semiconductor wafer between a wafer cassette and the process chamber. Semiconductor wafers contained within the wafer cassette are assigned numbers and processed one after another in a predetermined order. The wafer handling system is configurable to remove semiconductor wafers from the wafer cassette for processing in the predetermined order. One embodiment of the wafer handling system includes a mechanical hand for gripping a semiconductor wafer and a mechanical arm coupled to the mechanical hand for positioning the mechanical hand. The process chamber of the wafer fabrication tool may be, for example, a deposition chamber, an etch chamber, a spin coat chamber, a furnace, a diffusion chamber, an oxidation chamber, or an ion implantation chamber. In the present method, a unique wafer processing order is selected for each wafer fabrication tool, and each wafer fabrication tool is configured to implement the corresponding wafer processing sequence. Graphs of the number of contaminants (or defects) in the wafers verses wafer number generated for each of the wafer processing sequences may be analyzed to determine if one wafer fabrication tool introduced more contaminants into the wafers than the other wafer fabrication tools.

16 Claims, 4 Drawing Sheets

APPARATUS AND METHOD FOR SEMICONDUCTOR WAFER PROCESSING WHICH FACILITATE DETERMINATION OF A SOURCE OF CONTAMINANTS OR DEFECTS

BACKGROUND OF THE INVENTION

1. Field of the Invention

This invention relates to integrated circuit manufacturing and more particularly to semiconductor wafer handling associated with wafer fabrication.

2. Description of the Relevant Art

A typical modern wafer fabrication process forms multiple integrated circuits upon each of several semiconductor wafers processed one after another (i.e., sequentially). During wafer fabrication, multiple die areas are defined upon frontside surfaces of the semiconductor wafers. Integrated circuits are formed within these die areas using a series of wafer fabrication operations (e.g., layering, patterning, doping, and heat treatments). Following wafer fabrication, the dice are separated from the semiconductor wafers. Fully functional dice are typically mounted within semiconductor device packages and sold as individual units.

Due to the imperfect nature of all manufacturing processes, flaws or defects are introduced into integrated circuits during wafer fabrication. Sources of defects which adversely affect integrated circuit yield, performance, or reliability must be discovered and eliminated. Many such defects are caused by the introduction of one or more contaminants into integrated circuits during wafer fabrication operations. Such contaminants include small particles (i.e., particulates), heavy metal atoms, and mobile ionic contaminants.

Particulates are present in the ambient air, introduced by processing personnel, suspended in liquids and gasses used during processing, and generated by processing equipment. Particulates typically cause defects during layering and patterning operations. Particulates on the surface of a wafer may prevent the formation of a uniform layer of a desired material upon that surface. Such particulates also block or diffuse light during patterning operations (i.e., photolithography), causing imperfect pattern registrations resulting in imperfect feature formations.

Heavy metals include iron (Fe), copper (Cu), nickel (Ni), and gold (Au). Atoms of heavy metals form sites where minority and majority charge carriers have a tendency to recombine (i.e., recombination centers). As a result, minority carrier lifetimes are reduced. In general, long minority carrier lifetimes are beneficial to semiconductor device operation. Recombination centers which exist within regions near a surface of a semiconductor wafer where active devices reside (i.e., device active areas) thus represent defects as they lead to reduced minority carrier lifetimes.

Heavy metal contaminants may be derived from processing equipment during wafer fabrication. For example, many of the components which make up wafer fabrication tools are made of stainless steel, including ion implanters and gas and liquid delivery lines. Thus heavy metal atoms comprising stainless steel species may be introduced into semiconductor wafers during ion implantation and other wafer fabrication operations.

The presence of mobile ionic contaminants (e.g., sodium and potassium ions) in dielectric layers of metal oxide semiconductor (MOS) devices are known to cause device reliability problems. Mobile ionic contaminants are present in water and chemicals used during wafer fabrication, and also may be introduced by processing personnel. Ionized sodium ($Na^+$) and potassium ($K^+$) atoms are very mobile in oxide layers, and tend to move through gate oxides of MOS devices under the influence of the electric fields generated between gate electrodes and substrates during device operation. Long term changes in MOS device threshold voltage levels may occur as the charged ions drift to the interface between the gate oxide and the underlying substrate. Changes in threshold voltage levels may become large enough to cause circuits which incorporate these MOS devices to fail to meet electrical or performance requirements.

In order to determine the source of a given defect, test wafers are often included with wafers expected to yield operational integrated circuits (i.e., product wafers) and subjected to one or more wafer fabrication operations. Following the one or more wafer fabrication operations, the test wafers are separated from the product wafers and examined in an effort to determine the source of the defect. Such test wafers, however, represent a reduction in manufacturing yield as they do not produce operational devices.

An alternate approach to defect diagnosis which takes advantage of the sequential nature of modern wafer processing operations is to process the semiconductor wafers in a unique order through each wafer fabrication tool (e.g., deposition chamber, etch chamber, furnace, diffusion chamber, ion implantation device, etc.). Take, for example, a wafer fabrication tool which introduces contaminants into processed wafers. Due to sequential processing, the number of contaminants (or defects) in a given wafer corresponds to the order in which the wafer was processed through the wafer fabrication tool. A graph of contaminant (or defect) levels versus processed wafer number displays a consistent increasing contaminant (or defect) level trend. Thus if a group of wafers are processed through each of several wafer fabrication tools, and one of the wafer fabrication tool introduces more contaminants than the others, and the order in which each of the wafers is processed is unique for each wafer fabrication tool, then arrangement of the contaminant (defect) levels corresponding to each wafer in increasing order reveals the unique wafer processing sequence of the wafer fabrication tool which introduces the most contaminants.

A typical wafer fabrication facility includes multiple wafer fabrication tools which perform various wafer fabrication operations upon groupings of semiconductor wafers called "lots". The semiconductor wafers are typically transported within containers called wafer cassettes or wafer "boats". Each wafer cassette is configured to hold several wafers. Wafer fabrication tools typically incorporate wafer handling systems which remove wafers from cassettes for processing in a fixed order (e.g., first to last, top to bottom, etc.) and return processed wafers to their original positions within the cassettes.

The above approach to defect diagnosis is commonly implemented using special wafer fabrication tools called "wafer sorters" which do nothing but rearrange wafers within wafer cassettes so as to form unique orderings of the wafers within the cassettes. The unique orderings of the wafers within the cassettes are then recorded and associated with the wafer fabrication tool which is to process the wafers next, a necessary step in the above defect diagnosis approach. A wafer sorter must be visited prior to processing by each wafer fabrication tool. Multiple wafer sorters may thus be required to reduce processing bottlenecks. In addition to the initial costs of the wafer sorters, visits to wafer sorters add time to the overall wafer fabrication process and expose wafers to additional risks of damage or contamination.

It would thus be desirable to have a wafer fabrication tool which incorporates a wafer handling system capable of processing wafers within a wafer cassette in any order. Such desired wafer fabrication tools may be used to implement the above defect diagnosis approach which does not require test wafers or dedicated wafer sorters. The use of such desired wafer fabrication tools would also reduce overall wafer fabrication times as well as eliminate the additional risks of wafer damage or contamination associated with the wafer sorters.

SUMMARY OF THE INVENTION

The problems outlined above are in large part solved by an apparatus and method for performing a wafer fabrication operation upon each of a plurality of semiconductor wafers which facilitate determination of a source of semiconductor wafer contaminants or defects. A wafer fabrication tool of the present invention includes a process chamber for processing a semiconductor wafer and a wafer handling system for transporting the semiconductor wafer between a wafer cassette and the process chamber. Multiple semiconductor wafers to be processed are contained within the wafer cassette. Each of the semiconductor wafers is assigned a number, preferably corresponding to the position of the wafer within the cassette. The semiconductor wafers are processed by the wafer fabrication tool one after another, and the wafer handling system is configurable to remove semiconductor wafers from the wafer cassette in a predetermined order. A control unit of the wafer fabrication tool is coupled to both the process chamber and the wafer handling system. The control unit controls the actions of the process chamber and the wafer handling system, and is configurable to direct the removal of the semiconductor wafers from the wafer cassette in the predetermined order.

In one embodiment, the wafer handling system includes a mechanical hand for gripping a semiconductor wafer and a mechanical arm coupled to the mechanical hand for positioning the mechanical hand. The mechanical arm is used to insert the mechanical hand into the wafer cassette and to extract the mechanical hand and gripped semiconductor wafer from the wafer cassette. The wafer cassette is positioned such that the semiconductor wafers are stacked vertically. The wafer handling system also includes a vertical positioner coupled to the mechanical arm. The vertical positioner is used to vertically position the mechanical arm and attached mechanical hand with respect to the wafer cassette.

The process chamber of the wafer fabrication tool may be, for example, a deposition chamber, an etch chamber, a spin coat chamber, a furnace, a diffusion chamber, an oxidation chamber, or an ion implantation chamber. The wafer fabrication tool preferably includes mechanisms for controlling the temperature and pressure within the process chamber during use. The process chamber preferably includes gas inlet ports to allow entry of various gases during processing. Deposition and spin coat chambers are used to form a layer of a desired material upon at least one exposed surface of a semiconductor wafer contained therein. An etch process which removes portions of one or more layers from exposed surfaces of a semiconductor wafer may be carried out within an etch chamber. The process chamber may include one or more heat sources configured to heat a semiconductor wafer contained therein during use. The process chamber may contain a source of dopant atoms during use, or a stream of dopant ions may be introduced into the process chamber during use. A semiconductor wafer contained within the process chamber during use may thus be subjected to dopant atoms.

Numbers of contaminants (and resulting defects) within semiconductor wafers tend to increase with the number of wafers processed by a wafer fabrication tool which processes wafers sequentially and introduces defects into the processed wafers. This fact may be used to determine if one of the wafer fabrication tools introduced more contaminants than the other wafer fabrication tools. The present method for performing a wafer fabrication operation upon each of several semiconductor wafers facilitates determination of a source of semiconductor wafer contamination. One or more wafer fabrication tools are provided which perform wafer fabrication operations upon each of the several semiconductor wafers. The wafers are processed one after another and in a predetermined sequence by each wafer fabrication tool. The semiconductor wafers are preferably arranged with a wafer cassette, and each wafer is assigned a number corresponding to its position within the wafer cassette. A unique wafer processing sequence is selected for each processing tool. The wafer processing sequences may be selected using various means, including random selection. Prior to wafer processing by a given wafer fabrication tool, the wafer fabrication tool is configured to implement the corresponding wafer processing sequence.

Following processing by all of the wafer fabrication tools, each of wafers is inspected to determine the number of contaminants (or defects). The number of contaminants (or defects) in the wafers is then graphed verses wafer number for each of the wafer processing sequences used. A graph which shows a consistent increasing trend in the number of contaminants (or defects) versus wafer number for a given wafer processing sequence indicates that the corresponding wafer fabrication tool introduced more contaminants into the wafers than the other wafer fabrication tools.

BRIEF DESCRIPTION OF THE DRAWINGS

Other objects and advantages of the invention will become apparent upon reading the following detailed description and upon reference to the accompanying drawing which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 1:
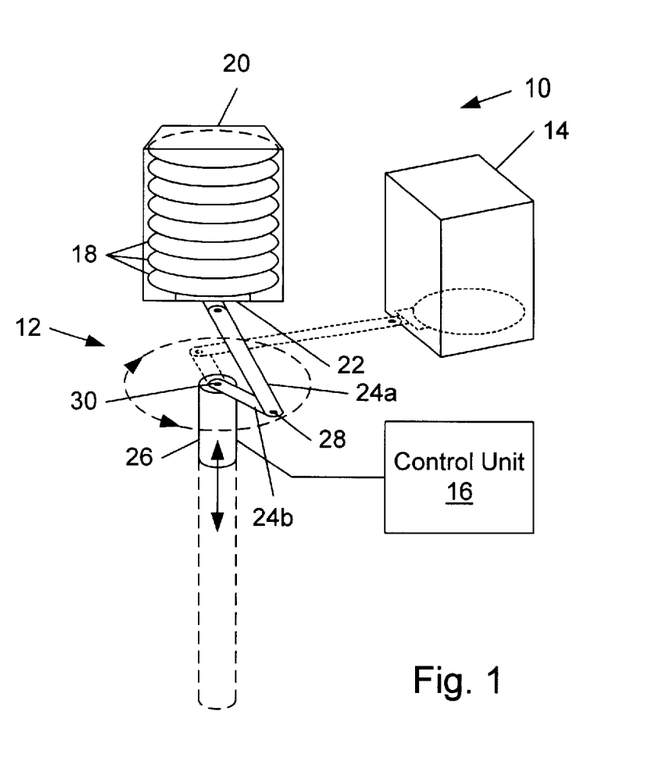
FIG. 1 is an isometric view of one embodiment of a wafer fabrication tool of the present invention, wherein the wafer fabrication tool includes a process chamber for processing a semiconductor wafer and a wafer handling system for transporting the semiconductor wafer between a wafer cassette and the process chamber, and wherein the wafer handling system includes a mechanical hand connected to a mechanical arm.

FIG. 1 is an isometric view of one embodiment of a wafer fabrication tool 10 of the present invention. Wafer fabrication tool 10 includes a wafer handling system 12, a process chamber 14, and a control unit 16. Process chamber 14 is used to perform a wafer fabrication operation upon a semiconductor wafer contained therein. Wafer handling system 12 is used to transfer semiconductor wafers 18 between a wafer cassette 20 and process chamber 14. Control unit 16 controls the actions of wafer handling system 12 and process chamber 14. Semiconductor wafers 18 are processed within process chamber 14 one after another (i.e., sequentially) and in a predetermined order. Prior to processing, wafer handling system 12 removes a semiconductor wafer 18 from wafer cassette 20 and places the semiconductor wafer 18 within process chamber 14. Following processing, wafer handling system 12 removes semiconductor wafer 18 from process chamber 14 and places semiconductor wafer 18 in its original location within wafer cassette 20.

Control unit 16 is configured in advance of the processing of semiconductor wafers 18 to process semiconductor wafers 18 in a prescribed order (i.e., sequence). Such configuration may be accomplished in various ways, including software programming or hardware programming. Software programming may involve, for example, saving the prescribed wafer processing sequence in a memory unit of control unit 16. Hardware programming may involve, for example, setting one or more switches or connecting wires between terminals of control unit 16 in order to implement the prescribed wafer processing sequence.

In the embodiment of FIG. 1, wafer cassette 20 contains several semiconductor wafers 18, and wafer cassette 20 is positioned such that semiconductor wafers 18 are stacked vertically within wafer cassette 20. Wafer handling system 12 includes a mechanical hand 22, an articulated mechanical arm 24 including a first arm section 24a and a second arm section 24b, and a vertical positioner 26. In FIG. 1, mechanical hand 22 is shown gripping the underside (i.e., backside) surface of the lower-most semiconductor wafer 18 within wafer cassette 20. Mechanical hand 22 is mounted at one end of mechanical arm 24, and the other end of mechanical arm 24 is attached to an upper end of vertical positioner 26. First arm section 24a and second arm section 24b of mechanical arm 24 are joined by an arm pin 28, forming a translational joint between first arm section 24a and second arm section 24b. The translational arm joint allows first arm section 24a and second arm section 24b to move about arm pin 28 in parallel planes.

Mechanical arm 24 is joined to vertical positioner 26 by a positioner pin 30. Vertical positioner 26 is able to move vertically through a hole in a working surface, allowing vertical positioning of mechanical arm 24 and mechanical hand 22 with respect to wafer cassette 20. A second translational joint is formed where second arm section 24b and vertical positioner 26 are joined by positioner pin 30. The second translational joint allows second arm section 24b to move about positioner pin 30 in a plane parallel to a flat upper surface of vertical positioner 26. By virtue of the joints described above, positioning of mechanical hand 22 is very flexible within limits determined by the lengths of first arm section 24a, second arm section 24b, and vertical positioner 26.

Figure 2:
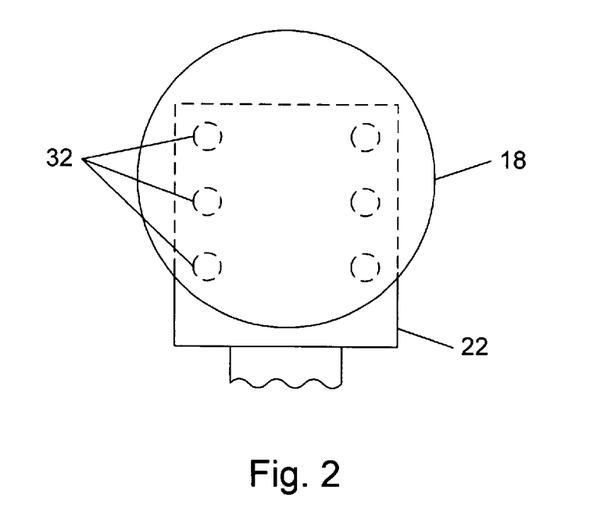
FIG. 2 is a top plan view of one embodiment of the mechanical hand of the wafer handling system of FIG. 1, wherein the mechanical hand is gripping an underside (i.e., a backside) surface of a semiconductor wafer.

FIG. 2 is a top plan view of one embodiment of mechanical hand 22 gripping the underside (i.e., backside) surface of semiconductor wafer 18. A flat upper surface of mechanical hand 22 includes multiple vacuum ports 32. Vacuum ports 32 are connected to a vacuum source through a valve. When gripping of semiconductor wafer 18 is required, the upper surface of mechanical hand 22 is placed in proximity of the backside surface of semiconductor wafer 18 and the valve is opened. As a result, a vacuum is formed between the upper surface of mechanical hand 22 and the backside surface of semiconductor wafer 18 which mechanically couples mechanical hand 22 and semiconductor wafer 18. When semiconductor wafer 18 is to be released, the valve is closed, and the vacuum loses strength until mechanical hand 22 and semiconductor wafer 18 are no longer mechanically coupled.

Process chamber 14 of FIG. 1 may be, for example, a deposition chamber, an etch chamber, a spin coat chamber, a furnace, a diffusion chamber, an oxidation chamber, or an ion implantation chamber. Wafer fabrication tool 10 preferably includes mechanisms for controlling the temperature and pressure within process chamber 14 during processing. Process chamber 14 preferably includes gas inlet ports to allow entry of various gases during processing. A deposition chamber is used to form a layer of a desired material upon exposed surfaces of a semiconductor wafer (e.g., silicon wafer). Representative examples of deposition chambers include chemical vapor deposition (CVD) chambers, vacuum evaporation chambers, and sputtering or physical vapor deposition (PVD) chambers. An etch chamber is used to remove portions of one or more layers from exposed surfaces of a semiconductor wafer. An etch chamber may employ a liquid etchant (i.e., implement a "wet" etch process) or reactive chemical species (i.e., implement a "dry" etch process). Examples of etch chambers which implement dry etch processes include barrel plasma etch chambers and planar plasma etch chambers.

A spin coat chamber is used to form a layer of a resist (e.g., photoresist) material over an exposed upper surface of semiconductor wafer 18. Semiconductor wafer 18 undergoing a spin coat process is typically held on a vacuum chuck within process chamber 14. A sufficient amount of liquid resist material is then deposited near the center of semiconductor wafer 18, and allowed to spread out into a puddle. When the puddle reaches a predetermined diameter, semiconductor wafer 18 and the vacuum chuck are sent into a rotating motion about an axis near the center of and normal to the upper surface of semiconductor wafer 18. The wafer and vacuum chuck are rapidly accelerated to a predetermined rotational speed. Centrifugal forces spread the resist material from the center of semiconductor wafer 18 to the edge of semiconductor wafer 18. Excess resist material is thrown off of the edge of semiconductor wafer 18. A substantially uniform layer of resist material is thus achieved across the exposed upper surface of semiconductor wafer 18.

Process chamber 14 may include one or more heat sources configured to heat semiconductor wafer 18 contained therein. A source of dopant atoms may be provided within process chamber 14, and process chamber 14 may thus function as a diffusion chamber. A flow of an oxygen-rich gas may be provided with process chamber 14, and process chamber 14 may thus function as an oxidation chamber. Wafer fabrication tool 10 may include a mechanism for producing a stream of ionized dopant atoms directed to semiconductor wafer 18 positioned within process chamber 14. Process chamber 14 may thus function as an ion implantation chamber.

Contaminant/defect levels introduced by a wafer fabrication tool which processes wafers sequentially and introduces contaminants/defects tend to increase with the number of wafers processed by the wafer fabrication tool. For example, contaminants may be formed within a process chamber of a wafer fabrication tool during processing. Some of the contaminants may end up on surfaces of processed wafers, and some may cling to surfaces of the process chamber. During future processing, a portion of the contaminants clinging to the walls of the process chamber may be released in addition to the new contaminants formed during processing. Thus as the number of processed wafers increases, the number of contaminants present within the process chamber increases. As a result, the number of contaminants which end up on processed wafers would be expected to increase with the number of wafers processed. This fact may be used to determine if one of several wafer fabrication tools introduced more contaminants than the remaining wafer fabrication tools.

Figure 3:
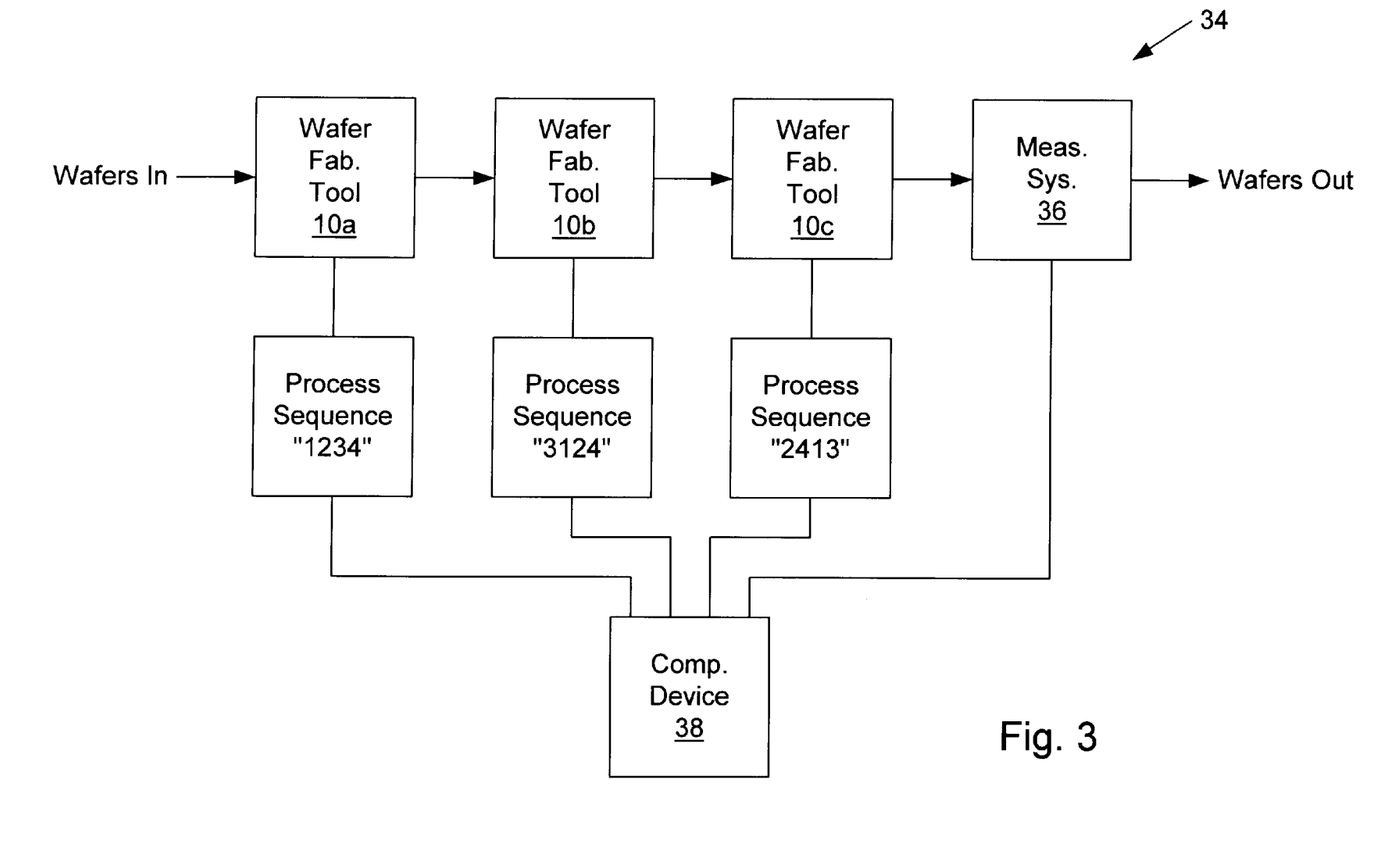
FIG. 3 is a block diagram of an exemplary wafer fabrication system for implementing a wafer contaminant/defect diagnostic approach, wherein the wafer fabrication system includes multiple wafer fabrication tools of FIG. 1, a measurement system for determining the number of contaminants/defects upon processed wafers, and a computational device for determining if one of the wafer fabrication tools introduced more contaminants/defects than the other wafer fabrication tools.

A working example will now be used to describe the operation of an exemplary wafer fabrication system 34 shown in FIG. 3. Exemplary wafer fabrication system 34 implements a wafer contaminant/defect diagnosis approach, and includes multiple wafer fabrication tools which process semiconductor wafers. Three wafer fabrication tools 10a–c are shown in FIG. 3, each of which is an instance of wafer fabrication tool 10 as described above. In addition to the multiple wafer fabrication tools, wafer fabrication system 34 includes a measurement system 36 and a computational device 38.

Measurement system 36 is used to measure the number of contaminants or defects upon surfaces of processed wafers. Measurements system 36 may be, for example, a laser-based system which optically determines the number of contaminants or defects upon surfaces of processed wafers. Computational device 38 is used to determine which of the wafer fabrication tools 10a–c is responsible for introducing more contaminants or defects upon the processed wafers than the other wafer fabrication tools. Computational device 38 may accomplish this by, for example, arranging the contaminant/defect levels of processed wafers in increasing order, then determining if the corresponding wafer numbers match the processing sequence of one of the wafer fabrication tools 10a–c. The existence of such a match indicates that the corresponding wafer fabrication tool introduced more contaminants/defects than any of the other wafer fabrication tools. Computational device 38 may also be used to select the wafer processing sequences for wafer fabrication tools 10a–c.

A group of four semiconductor wafers are processed through wafer fabrication tools 10a–c in sequence. The four semiconductor wafers are contained within a single wafer cassette. Each of the four semiconductor wafers is assigned a number, preferably corresponding to its position within the wafer cassette, and the original order of the wafers within the wafer cassette is maintained during processing. Prior to the processing of the four wafers by wafer fabrication tool 10a, control unit 16 of wafer fabrication tool 10a is configured to process the four semiconductor wafers in some predetermined order. The processing sequence for wafer fabrication unit 10a may be determined by various means, including random selection. Once the processing sequence has been selected for wafer fabrication tool 10a, wafer fabrication tools 10b and 10c are barred from using the same processing sequence. The selected processing sequence for wafer fabrication tool 10a may be, for example, the sequence "1 2 3 4", wherein wafer "1" is the first wafer processed, followed by wafer "2", and so on until all four wafers have been processed by wafer fabrication tool 10a.

Once control unit 16 of wafer fabrication tool 10a has been configured to process the four semiconductor wafers in processing order "1 2 3 4", processing of the four semiconductor wafers by wafer fabrication tool 10a may begin. Wafer handling system 12 of wafer fabrication tool 10a removes the semiconductor wafer numbered "1" from the wafer cassette and places the semiconductor wafer numbered "1" within process chamber 14 of wafer fabrication tool 10a. Following processing of the semiconductor wafer numbered "1", wafer handling system 12 of wafer fabrication tool 10a returns the semiconductor wafer numbered "1" to its original position within the wafer cassette, removes the semiconductor wafer numbered "2" from the wafer cassette, and places the semiconductor wafer numbered "2" within process chamber 14 of wafer fabrication tool 10a. The processing sequence "1 2 3 4" is continued until the semiconductor wafer numbered "4" is processed and returned to its original location within the wafer cassette. Processing of the four wafers by wafer fabrication tool 10a is now complete.

Prior to the processing of the four wafers by wafer fabrication tool 10b, control unit 16 of wafer fabrication tool 10b is configured to process the four semiconductor wafers in a predetermined order. The processing sequence for wafer fabrication unit 10b is selected such that it differs from the processing sequence selected for wafer fabrication tool 10a. As before, various means may be used to determine the processing sequence, including random selection. The selected processing sequence for wafer fabrication tool 10b may be, for example, the sequence "3 1 2 4".

Once control unit 16 of wafer fabrication tool 10b has been configured to implement processing sequence "3 1 2 4", processing of the four semiconductor wafers may begin. Wafer handling system 12 of wafer fabrication tool 10b removes the semiconductor wafer numbered "3" from the wafer cassette and places the semiconductor wafer numbered "3" within process chamber 14 of wafer fabrication tool 10b. Following processing of the semiconductor wafer numbered "3", wafer handling system 12 of wafer fabrication tool 10b returns the semiconductor wafer numbered "3" to its original position within the wafer cassette, removes the semiconductor wafer numbered "1" from the wafer cassette, and places the semiconductor wafer numbered "1" within process chamber 14 of wafer fabrication tool 10b. The processing sequence "3 1 2 4" is continued until the semiconductor wafer numbered "4" is processed and returned to its original location within the wafer cassette. Processing of the four wafers by wafer fabrication tool 10b is now complete.

Control unit 16 of wafer fabrication tool 10c is configured to process the four semiconductor wafers in a predetermined order which differs from the processing sequence selected for wafer fabrication tools 10a and 10b. The selected processing sequence for wafer fabrication tool 10c may be, for example, the sequence "2 4 1 3". Wafer fabrication is complete when wafer fabrication tool 10c finishes processing wafer "3".

Measurements system 36 is used to determine the number of contaminants (or defects) present upon each of the four wafers. Measurement system 36 forwards wafer numbers and corresponding contaminant/defect counts to computational device 38. Computational device 38 may arrange the contaminant/defect levels of the four wafers in increasing order, then determine if the corresponding wafer number order matches the wafer processing sequence of one of the wafer fabrication tools 10a–c. The existence of such a match indicates that the corresponding wafer fabrication tool introduced more contaminants/defects than any of the other wafer fabrication tools. Alternately, computational device 38 may generate graphs of the number of contaminants (or defects) in the four wafers verses wafer number for each wafer processing sequence used. These graphs may then be used to determine if one of the wafer fabrication tools 10a–c introduced more contaminants into the wafers than the others. A consistent increasing trend in a graph of the number of contaminants/defects in processed wafers verses wafer number for a wafer processing sequence indicates that the corresponding wafer fabrication tool introduced more contaminants/defects than any of the other wafer fabrication tools. Table 1 below lists example contaminant/defect counts for each of the four wafers.

TABLE 1

Example Contaminant/Defect Counts for Four Processed Wafers.

| Wafer No. | Contaminant/Defect Count |
|---|---|
| 1 | 42 |
| 2 | 64 |
| 3 | 25 |
| 4 | 100 |

Figure 4A:
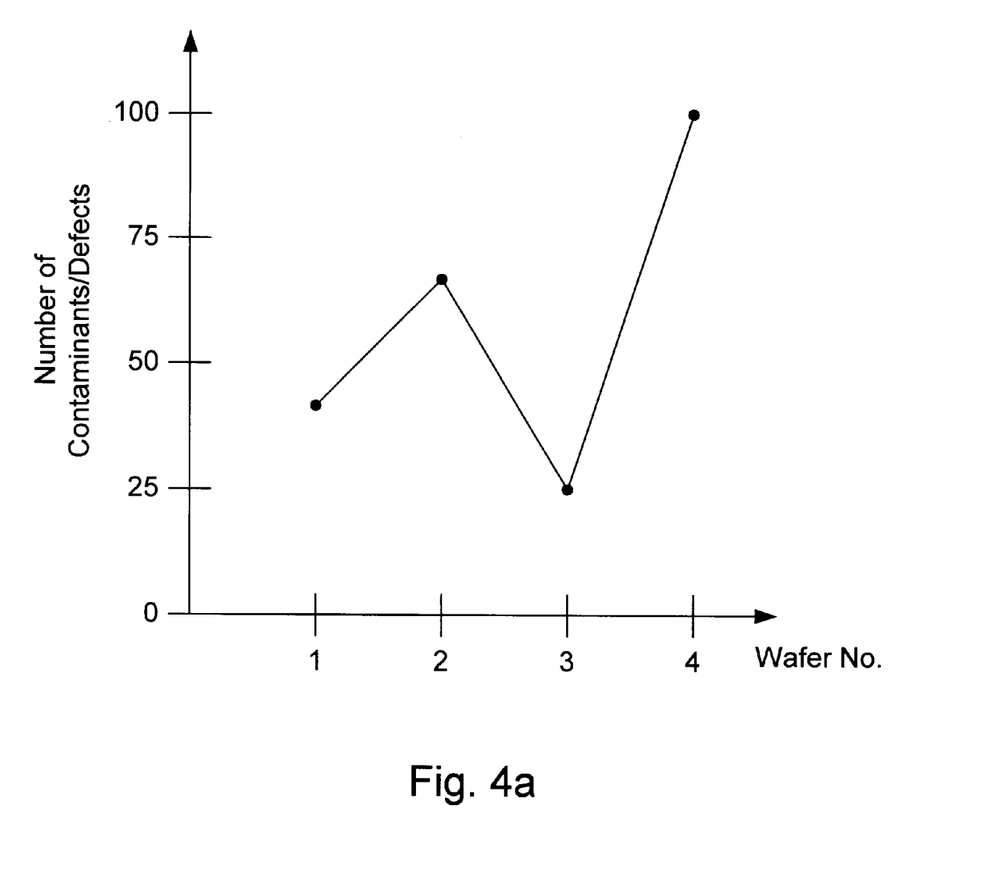
FIG. 4a is a graph of the number of contaminants/defects versus wafer number for a wafer processing sequence "1 2 3 4" used by a first wafer fabrication tool of FIG. 3.

FIG. 4a is a graph of the number of contaminants/defects versus wafer number for processing sequence "1 2 3 4" used by wafer fabrication tool 10a. Since wafer number "3" has fewer contaminants/defects than wafer numbers "2" and "4", a "dip" occurs in the graph corresponding to wafer number "3", and no consistent increasing pattern is noted in the graph. The lack of a consistent increasing pattern leads to the determination that wafer fabrication tool 10a did not introduce more contaminants than wafer fabrication tools 10b or 10c.

Figure 4B:
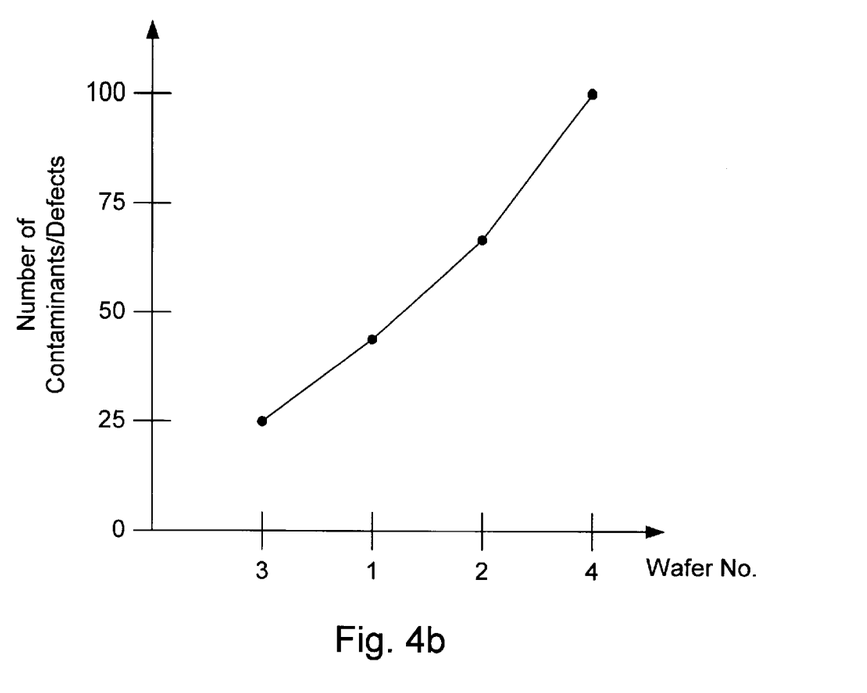
FIG. 4b is a graph of the number of contaminants/defects versus wafer number for a wafer processing sequence "3 1 2 4" used by a second wafer fabrication tool of FIG. 3.

FIG. 4b is a graph of the number of contaminants/defects versus wafer number for processing sequence "3 1 2 4" used by wafer fabrication tool 10b. Since arrangement of the contaminant/defect levels of each wafer in increasing order matches the processing order of wafer fabrication tool 10b, the graph of FIG. 4b displays a consistent increasing trend. This consistent increasing pattern leads to the determination that wafer fabrication tool 10b introduced more contaminants than wafer fabrication tools 10a or 10c.

Figure 4C:
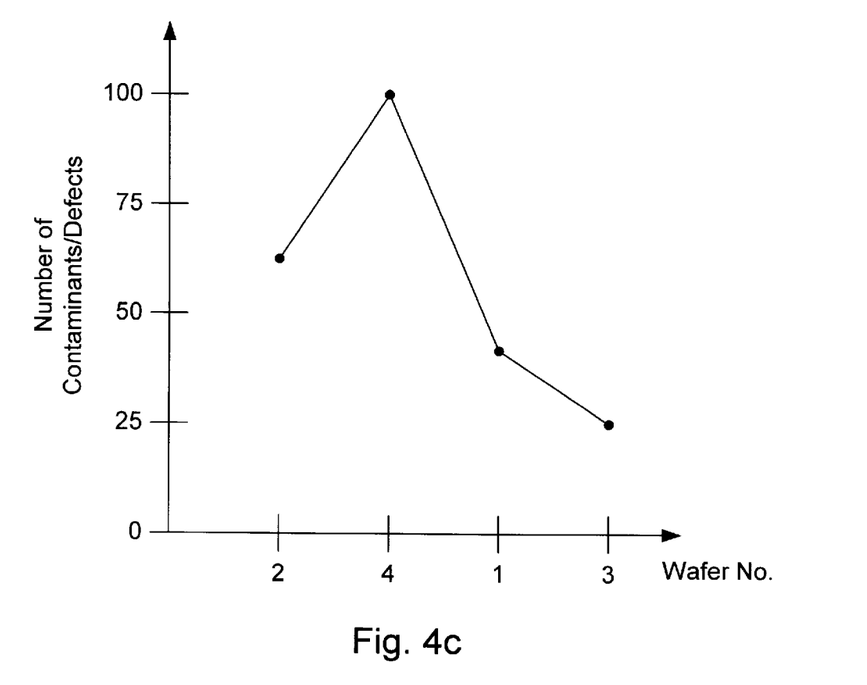
FIG. 4c is a graph of the number of contaminants/defects versus wafer number for a wafer processing sequence "2 4 1 3" used by a third wafer fabrication tool in FIG. 3.

FIG. 4c is a graph of the number of contaminants/defects versus wafer number for processing sequence "2 4 1 3" used by wafer fabrication tool 10c. Since wafer numbers "1", "2", and "3" have fewer contaminants/defects than wafer number "4", a "peak" occurs in the graph corresponding to wafer number "4", and no consistent increasing pattern is noted in the graph. As a consistent increasing pattern is not present, it is determined that wafer fabrication tool 10c did not introduce more contaminants than wafer fabrication tools 10a or 10b. This determination is consistent with the above findings.

It will be appreciated by those skilled in the art having the benefit of this disclosure that this invention is believed to be an apparatus and method for performing a wafer fabrication operation upon each of a plurality of semiconductor wafers which facilitate determination of a source of semiconductor wafer contaminants or defects. Furthermore, it is also to be understood that the form of the invention shown and described is to be taken as exemplary, presently preferred embodiments. Various modifications and changes may be made without departing from the spirit and scope of the invention as set forth in the claims. It is intended that the following claims be interpreted to embrace all such modifications and changes.

What is claimed is:

1. A wafer fabrication system, comprising:
    a wafer cassette configured to hold a plurality of semiconductor wafers;
    a plurality of wafer fabrication tools configured to receive said wafer cassette and to process said plurality of semiconductor wafers, wherein each one of said plurality of wafer fabrication tools is configured to process said plurality of semiconductor wafers in a different order than the other ones of said plurality of wafer fabrication tools, wherein an original order of said plurality of semiconductor wafers is maintained in said wafer cassette during processing by said plurality of wafer fabrication tools; and
    a measurement system configured to determine a quantity of contaminants or defects present upon each of said plurality of semiconductor wafers after processing by said plurality of wafer fabrication tools.

2. The system as recited in claim 1, further comprising a computational device configured to receive said quantity from said measurement system for each of said plurality of semiconductor wafers and to determine which one of said plurality of wafer fabrication tools may have introduced more contaminants or defects than any of the other ones of said plurality of wafer fabrication tools.

3. The system as recited in claim 2, wherein said computational device is configured to order said quantity for each of said plurality of semiconductor wafers in increasing order and compare that order to each different order that said plurality of semiconductor wafers was processed by said plurality of wafer fabrication tools.

4. The system as recited in claim 1, wherein each one of said plurality of wafer fabrication tools comprises:
    a process chamber;
    a wafer handling system configured to transfer ones of said plurality of semiconductor wafers from said wafer cassette to said process chamber; and
    a control unit configured to control the order in which said wafer handling system transfers ones of said plurality of semiconductor wafers from said wafer cassette to said process chamber, wherein said control unit is programmed to control said wafer handling system so that said plurality of semiconductor wafers are transferred from said wafer cassette to said process chamber in a different order than in the other ones of said plurality of wafer fabrication tools, and wherein said original order of said plurality of semiconductor wafers is maintained in said wafer cassette.

5. The system as recited in claim 4, wherein the process chamber for one of said plurality of wafer fabrication tools comprises a deposition chamber.

6. The system as recited in claim 4, wherein the process chamber for one of said plurality of wafer fabrication tools comprises an etch chamber.

7. The system as recited in claim 4, wherein the process chamber for one of said plurality of wafer fabrication tools comprises a spin coat chamber.

8. The system as recited in claim 4, wherein the process chamber for one of said plurality of wafer fabrication tools comprises a heating chamber.

9. The system as recited in claim 4, wherein the process chamber for one of said plurality of wafer fabrication tools comprises a diffusion chamber.

10. The system as recited in claim 4, wherein the process chamber for one of said plurality of wafer fabrication tools comprises an oxidation chamber.

11. The system as recited in claim 4, wherein the process chamber for one of said plurality of wafer fabrication tools comprises an implantation chamber.

12. The system as recited in claim 1, wherein said different order is selected randomly so long as said different order for each one of said plurality of wafer fabrication tools is different than for the other ones of said plurality of wafer fabrication tools.

13. A wafer fabrication method, comprising:
    processing a group of semiconductor wafers from a wafer cassette in a plurality of wafer fabrication tools, wherein said group of semiconductor wafers is processed in a different order for each one of said plurality of wafer fabrication tools than for the other ones of said plurality of wafer fabrication tools;
    maintaining an original order of said group of semiconductor wafers in said wafer cassette during said processing for all of said plurality of wafer fabrication tools; and
    measuring a quantity of contaminants or defects present upon each of said group of semiconductor wafers after said processing; and
    determining which one of said plurality of wafer fabrication tools may have introduced more contaminants or defects than any of the other ones of said plurality of wafer fabrication tools.

14. The method as recited in claim 13, wherein said determining comprises:
    ordering said quantity for each of said group of semiconductor wafers in increasing order; and
    comparing that order to each different order that said group of semiconductor wafers was processed by said plurality of wafer fabrication tools.

15. The method as recited in claim 13, further comprising, prior to said processing, programming a control unit for each of said plurality of wafer fabrication tools to control a wafer handling system for each of said plurality of wafer fabrication tools so that said group of semiconductor wafers are transferred during said processing from said wafer cassette to a process chamber for each of said plurality of wafer fabrication tools in a different order than in the other ones of said plurality of wafer fabrication tools, and wherein said original order of said group of semiconductor wafers is maintained in said wafer cassette during said processing.

16. The method as recited in claim 13, further comprising selecting said different order randomly so long as said different order for each one of said plurality of wafer fabrication tools is different than for the other ones of said plurality of wafer fabrication tools.

* * * * *